(12) United States Patent
Dockner et al.

(10) Patent No.: US 7,265,238 B2
(45) Date of Patent: Sep. 4, 2007

(54) PROCESS FOR PREPARING METHYL 4-(AMINOMETHYL)BENZOATE

(75) Inventors: Michael Dockner, Köln (DE); Torsten Neugebauer, Bad Honnef (DE)

(73) Assignee: Saltigo GmbH, Leverkusen (DE)

( * ) Notice: Subject to any disclaimer, the term of this patent is extended or adjusted under 35 U.S.C. 154(b) by 0 days.

(21) Appl. No.: 11/525,279

(22) Filed: Sep. 22, 2006

(65) Prior Publication Data

US 2007/0149802 A1    Jun. 28, 2007

(30) Foreign Application Priority Data

Sep. 28, 2005    (DE) ...................... 10 2005 046 343

(51) Int. Cl.
C07C 229/00    (2006.01)
C07C 67/08    (2006.01)
C07C 69/00    (2006.01)

(52) U.S. Cl. ........................... 560/19; 560/98; 560/129

(58) Field of Classification Search .................... None
See application file for complete search history.

(56) References Cited

U.S. PATENT DOCUMENTS 6,172,084 B1    1/2001    Cuny et al. ................. 514/312

FOREIGN PATENT DOCUMENTS

| JP | 1972-0075050 | 3/1974 |
|---|---|---|
| JP | 1973-0136140 | 7/1975 |
| JP | 1977-0104929 | 4/1979 |
| JP | 1979-0085926 | 2/1981 |
| SU | 1989-4670483 | 7/1991 |

OTHER PUBLICATIONS

Umino, Norihide, et al., "Sodium Acyloxyborohydride as New Reducing Agents. II. Reduction of Nitriles to the corresponding Amines"; *Tetrahedron Letters* No. 33, pp. 2875-2876, (1976).

Heinzman, Stephen W., et al., "The Mechanism of Sodium Borohydride-Cobaltous Chloride Reductions"; *J. Am. Chem. Soc.* 1982, 104, pp. 6801-6802.

Suzuki, Hitomi, et al., "A Chemoselective Conversion of Alkyl and Aryl Azides to Amines with Sodium Hydrogentelluride", *Chemistry Letters* 1984, p. 1733.

Takamizawa, Satoshi, et al., "Supported Nickel-Catalyzed Hydrogenation of Aromatic Nitriles under Low Pressure Conditions", *Synlett 2001*, No. 10, p. 1623.

Primary Examiner—Sikarl A. Witherspoon
(74) Attorney, Agent, or Firm—Michael A. Miller

(57) ABSTRACT

An advantageous process is provided for preparing methyl 4-(aminomethyl)benzoate by esterifying 4-(aminomethyl) benzoic acid and subsequently obtaining the methyl 4-(aminomethyl)benzoate, this process proceeding under specific pH and temperature control and isolation of the hydrochloride of methyl 4-(aminomethyl)benzoate formed as an intermediate being avoidable.

14 Claims, No Drawings

PROCESS FOR PREPARING METHYL 4-(AMINOMETHYL)BENZOATE

This application claims the benefit of German Application No. DE 10 2005 046 343.5 filed Sep. 28, 2005.

FIELD OF THE INVENTION

The present invention relates to a process for preparing methyl 4-(aminomethyl)benzoate by esterifying 4-(aminomethyl)benzoic acid and subsequently obtaining the methyl 4-(aminomethyl)benzoate under specific pH and temperature control.

BACKGROUND OF THE INVENTION

The esters of 4-(aminomethyl)benzoic acid are intermediates for the synthesis of active pharmaceutical ingredients. Since methyl esters can easily be hydrolyzed again, methyl 4-(aminomethyl)benzoate is of interest when mild conditions for the release of the acid function are sought in a synthesis sequence for the active ingredient.

For the preparation of methyl 4-(aminomethyl)benzoate, the literature already discloses various routes.

Methyl 4-(aminomethyl)benzoate is obtainable via the catalytic hydrogenation of methyl 4-cyanobenzoate (Synlett 10, 1623 (2001)), of the oxime (JP 1979-85926, JP 1973-136140) which is obtained from methyl 4-formylbenzoate and hydroxylamine, or of the imine formed from methyl 4-formylbenzoate and ammonia (JP 1977-104929).

In addition to hydrogen, it is also possible to use sodium borohydride in conjunction with cobalt(II) chloride (J. Am. Chem. Soc. 104, 6801 (1982)) or trifluoroacetic acid (Tetrahedron Lett. 33, 2875 (1976)) to reduce the 4-nitrile group or 4-amido group of the methyl benzoate.

SU 1989-4670483 also discloses that the para-amido group can also be reduced electrochemically to give the aminomethylene group.

Chem. Lett. 10, 1733 (1984) describes 4-methoxycarbonylbenzyl azide as a starting compound from which methyl 4-(aminomethyl)benzoate is obtained by treating with sodium hydrogen telluride.

It is likewise possible to synthesize methyl 4-(aminomethyl)benzoate by a chlorine/amine exchange on methyl parachloromethylbenzoate in nonaqueous media (JP 1972-75050).

In all aforementioned methods, the desired methyl ester group in the particular starting compound is already present. Owing to the reaction conditions, some of which are harsh, the methyl ester is, however, hydrolyzed again in an undesired manner actually during the reaction or the workup.

It is also possible, for the synthesis of the 4-(aminomethyl)benzoic ester, to start from the 4-(aminomethyl)benzoic acid available in commercial amounts and to esterify it with the corresponding alcohol.

J. Med. Chem. 37, (1994) discloses the esterification in the presence of hydrochloric acid in methanol boiling at reflux. However, the product is obtained as the hydrochloride and, owing to its corrosive properties, this greatly restricts the apparatus selection for the isolation of the solid.

In U.S. Pat. No. 6,172,084, instead of hydrochloric acid, hydrogen chloride is introduced into the methanolic reaction mixture, and the 4-(aminomethyl)benzoic acid is esterified by heating at reflux overnight. The reaction mixture is subsequently concentrated, admixed with saturated aqueous sodium carbonate solution and extracted three times with methylene chloride. The combined organic phases are dried with magnesium sulphate, freed of the desiccant by filtration and subsequently concentrated. Performance by this method on the industrial scale is not possible, since large amounts of magnesium sulphate are obtained, and are expensive to dispose of. Moreover, the yield achieved according to U.S. Pat. No. 6,172,084 is only about 57%.

The latter two methods for preparing methyl 4-(aminomethyl)benzoate are not satisfactory for performance on the industrial scale with regard to apparatus selection and ecological points of view. Moreover, the direct use of the hydrochloride obtained according to J. Med. Chem. 37, (1994) in a subsequent stage is not always possible and, in such cases, necessitates the preceding release in a further separate step, which impairs the economic attractiveness of the overall process. There is therefore a need for an easy-to-perform, economically viable and ecologically uncritical process for preparing 4-(aminomethyl)benzoic esters which is available for broad application.

SUMMARY OF THE INVENTION

It has been found that, surprisingly, the preparation of methyl 4-(aminomethyl)benzoate, which is performed starting from 4-(aminomethyl)benzoic acid by esterification in the presence of hydrochloric acid, is also possible without intermediate isolation of the hydrochloride, provided that the reaction mixture is worked up and the methyl 4-(aminomethyl)benzoate is obtained under specific process conditions.

DETAILED DESCRIPTION OF THE INVENTION

The invention thus provides a process for preparing methyl 4-(aminomethyl)benzoate by esterifying 4-aminomethylbenzoic acid with methanol in the presence of hydrochloric acid, characterized in that the reaction mixture resulting after the reaction with methanol 1) is first adjusted to a temperature in the range from −15 to +10° C. and, by adding a base, to a pH in the range from 4 to 9,
2) is subsequently concentrated and an organic solvent is added,
3) then the pH of the aqueous phase is adjusted to a value in the range from 9 to 12 by further addition of a base and
4) the organic phase which comprises the methyl 4-(aminomethyl)benzoate of the general formula (1) is removed.

For the successful performance of the process according to the invention, it is essential that the reaction mixture which results after the reaction of the 4-(aminomethyl)benzoic acid with methanol is cooled to a temperature in the range from −15 to +10° C., preferably in the range from +5 to +10° C.

It is also essential that the reaction mixture at this temperature in the range from −15 to +10° C., preferably from +5 to +10° C., is adjusted to a pH in the range from 4 to 9. This is affected typically by adding a water-soluble base. The mixture is preferably adjusted to a pH in the range from 5 to 8, more preferably of from 6.0 to 7.0.

Useful water-soluble bases for the adjustment of the pH are in principle water-soluble tertiary amines, and alkali metal and alkaline earth metal oxides, alkali metal and alkaline earth metal hydroxides, alkali metal and alkaline earth metal carbonates, alkali metal and alkaline earth metal hydrogen phosphates, and alkali metal and alkaline earth metal phosphates. Preference is given to using sodium hydroxide or potassium hydroxide.

The concentration of the base is freely variable and may, for example, be 2 to 50% by weight. Preference is given to aqueous 4 to 6% by weight solutions of sodium hydroxide or potassium hydroxide. Tertiary amines can also be used as such, i.e. without water.

After the pH adjustment, the reaction mixture is concentrated by distillation under reduced pressure. The pressure should preferably be adjusted such that the internal temperature in the reaction mixture does not exceed 40° C. For example, at the start of concentration, a pressure of 200 mbar can be selected, and, in the further course, lowered to 40 mbar. The internal temperature under these conditions is in the range from 17 to 33° C.

Subsequently, an organic solvent is added to the remaining reaction mixture, the concentrate.

The organic solvents used may be polar, water-immiscible solvents. Suitable examples are aromatic hydrocarbons such as toluene, and halogenated saturated hydrocarbons such as methylene chloride.

When toluene or other aromatic hydrocarbons are used, it is sensible to saturate the aqueous phase, preferably with sodium chloride or other salts, in order to extract the methyl 4-(aminomethyl)benzoate with high yield into the organic phase.

The organic solvent used is preferably methylene chloride.

After the addition of the solvent, it is important to adjust the pH of the aqueous phase of the resulting biphasic mixture to a value in the range from 9 to 12. This is affected typically by adding a water-soluble base. Preference is given to adjusting the mixture to a pH in the range from 9 to 11, more preferably in the range from 10.0 to 11.0.

Useful water-soluble bases are in principle water-soluble alkali metal or alkaline earth metal oxides, alkali metal or alkaline earth metal hydroxides, alkali metal or alkaline earth metal carbonates, alkali metal or alkaline earth metal hydrogen phosphates and alkali metal and alkaline earth metal phosphates. Preference is given to using sodium hydroxide or potassium hydroxide. It is advantageous to use the same base as in the adjustment of the pH in step 1) of the process according to the invention.

The concentration of the base is freely variable and may, for example, be 2 to 50% by weight. Preference is given to aqueous 4 to 6% by weight solutions of potassium hydroxide or sodium hydroxide.

The water-soluble base is added, for example, at a temperature of the reaction mixture in the range from −15 to +10° C., preferably from +5 to +10° C.

After the aforementioned pH adjustment, the organic phase which comprises the desired product in the form of the optionally substituted 4-(aminomethyl)benzoic ester of the general formula (1) is removed. A second extraction with the solvent used beforehand can but need not be effected.

Before the removal of the organic phase, the saturation of the aqueous phase with sodium chloride or other salts can help to convert the 4-(aminomethyl)benzoic ester of the formula (1) more efficiently to the organic phase. This is helpful especially when the organic solvent used is toluene or other aromatic hydrocarbons.

As a result of the specific process control during the workup of the reaction mixture after the esterification, it is possible in the process according to the invention to suppress the undesired and premature hydrolysis of the methyl 4-(aminomethyl)benzoate and, under the selected extraction conditions, also to ensure optimal conversion of the desired product to the organic phase. The methyl 4-(aminomethyl)benzoate can therefore be obtained in the process according to the invention in excellent yields of over 85% based on the 4-(aminomethyl)benzoic acid used. The yields achieved are preferably 88% or higher.

In the process according to the invention, in contrast to the process known from U.S. Pat. No. 6,178,084, drying of the organic phase after step 4) is advantageously not required. The occurrence of amounts of desiccant which are costly and inconvenient to dispense with can thus be avoided.

The process according to the invention affords the methyl 4-(aminomethyl)benzoate of the general formula (1) dissolved in an organic solvent without intermediate isolation of the hydrochloride formed as an intermediate and in this way also avoids restriction of the apparatus selection.

Moreover, methyl 4-(aminomethyl)benzoate is more widely useable than the corresponding hydrochloride.

It is possible to use the organic solution of the methyl 4-(aminomethyl)benzoate directly in a subsequent stage. It is also possible to undertake a solvent exchange beforehand. When the solvent of the organic solution is methylene chloride, for example, a change to higher-boiling solvents such as toluene is possible without any problem.

When there is no immediate direct further processing, it has been found to be useful to store this organic solution at 0 to 5° C. in order to suppress oligomerization.

The process according to the invention can be utilized advantageously in order to react the resulting methyl 4-(aminomethyl)benzoate with cyclohexenylchlorobenzene in a Buchwald C-N coupling. According to U.S. Pat. No. 6,172,084, the methyl 4-(aminomethyl)benzoate can also be used advantageously for the development of antibiotics based on quinoline and indole.

EXAMPLE

In a 1200 l stirred vessel made of steel and enamel, 60 kg of 4-(aminomethyl)benzoic acid, 480 kg of methanol and 89 kg of 30% hydrochloric acid are heated to boiling at reflux. After a reaction time of 7 h, the reaction mixture is cooled to 10° C.

Addition of 290 kg of 4% sodium hydroxide solution initially adjusts the pH of the reaction mixture to a pH of 6-7, before a methanol/water mixture is distilled off under reduced pressure.

Subsequently, 400 kg of methylene chloride are added and the pH of the aqueous phase is adjusted to a value of 10-11 at a temperature of 5-10° C.

The lower organic phase is removed. The aqueous phase is extracted once more with 265 kg of methylene chloride.

The organic phases are combined and stored at 0-5° C.

The content of the solution is determined by means of quantitative HPLC chromatography. The yield of methyl 4-(aminomethyl)benzoate is 88-89%.

What is claimed is:

1. A process for preparing methyl 4-(aminomethyl)benzoate comprising esterifying 4-aminomethylbenzoic acid with methanol in the presence of hydrochloric acid, wherein the reaction mixture resulting after the esterification reaction with methanol
   1) is first adjusted to a temperature in the range from −15 to +10° C. and, by adding a base, to a pH in the range from 4 to 9,
   2) is subsequently concentrated and an organic solvent is added,
   3) then the pH of the aqueous phase is adjusted to a value in the range from 9 to 12 by further addition of a base and 4) the organic phase which comprises the methyl 4-(aminomethyl)benzoate is removed.

2. The process according to claim 1, wherein the reaction mixture in step 1) is adjusted to a temperature in the range from 5 to +10° C. and a pH in the range from 5 to 8.

3. The process according to claim 1, wherein the reaction mixture in step 1) is adjusted to a temperature in the range from 5 to +10° C. and a pH in the range from 6.0 to 7.0.

4. The process according to claim 1, wherein the adjustment of the pH in step 1) is carried out by adding a water-soluble tertiary amine, alkali metal or alkaline earth metal oxides, alkali metal or alkaline earth metal hydroxides, alkali metal or alkaline earth metal carbonates, alkali metal or alkaline earth metal hydrogen phosphates, or alkali metal or alkaline earth metal phosphates.

5. The process according to claim 1, wherein the adjustment of the pH in step 1) is carried out by adding sodium hydroxide or potassium hydroxide.

6. The process according to claim 1, wherein the organic solvent used in step 2) is a polar, water-immiscible solvent.

7. The process according to claim 6, wherein the organic solvent used in step 2) is an aromatic hydrocarbon or a halogenated saturated hydrocarbon.

8. The process according to claim 6, wherein the organic solvent used in step 2) is toluene or methylene chloride.

9. The process according to claim 1, wherein the pH of the aqueous phase of the biphasic mixture of step 2) is adjusted in step 3) to a value in the range from 9 to 11.

10. The process according to claim 9, wherein the pH of the aqueous phase of the biphasic mixture of step 2) is adjusted in step 3) to a value in the range from 10.0 to 11.0.

11. The process according to claim 10, wherein the pH of the aqueous phase of the biphasic mixture of step 2) is adjusted in step 3) by adding as base a water-soluble alkali metal or alkaline earth metal oxide, alkali metal or alkaline earth metal hydroxide, alkali metal or alkaline earth metal carbonate, alkali metal or alkaline earth metal hydrogen phosphate, or alkali metal or alkaline earth metal phosphate.

12. The process according to claim 11, wherein the pH of the aqueous phase of the biphasic mixture of step 2) is adjusted in step 3) by adding sodium hydroxide or potassium hydroxide.

13. The process according to claim 1, wherein the organic phase which comprises the methyl 4-(aminomethyl)benzoate and which is removed after step 4) is not dried.

14. The process according to claim 1, wherein the organic phase from step 4) which comprises the methyl 4-(aminomethyl)benzoate is used as a reactant either after a solvent exchange or directly in a subsequent chemical reaction.

* * * * *